United States Patent [19]
Kujawski

[11] Patent Number: 5,284,138
[45] Date of Patent: Feb. 8, 1994

[54] APPARATUS AND METHOD FOR POSITIONING A SENSOR AWAY FROM THE BLOOD VESSEL WALL

[75] Inventor: Dennis Kujawski, Brookline, N.H.
[73] Assignee: C. R. Bard, Inc., Murray Hill, N.J.
[21] Appl. No.: 727,573
[22] Filed: Jul. 9, 1991
[51] Int. Cl.$^5$ .............................................. A61B 5/00
[52] U.S. Cl. .................................. 128/634; 128/673; 128/691
[58] Field of Search ............... 128/632, 634, 685, 637, 128/673–675, 691, 689, 692, 662.06, 419 PG

[56] References Cited

U.S. PATENT DOCUMENTS

| | | |
|---|---|---|
| Re. 27,310 | 3/1972 | Hakim . |
| 3,335,715 | 9/1964 | Hugenholtz et al. . |
| 3,405,708 | 10/1968 | Webster, Jr. . |
| 3,498,286 | 3/1970 | Polanyi et al. . |
| 3,529,591 | 9/1970 | Schuette . |
| 3,545,428 | 12/1970 | Webster, Jr. . |
| 3,674,013 | 7/1972 | Polanyi . |
| 3,807,390 | 4/1974 | Ostrowski et al. . |
| 3,866,599 | 2/1975 | Johnson . |
| 3,918,456 | 11/1975 | Patel . |
| 4,311,138 | 1/1982 | Sugarman . |
| 4,576,772 | 3/1986 | Carpenter . |
| 4,706,677 | 11/1987 | Goorsky et al. . |
| 4,733,669 | 3/1988 | Segal . |
| 4,785,814 | 11/1988 | Kane . |
| 4,830,013 | 5/1989 | Maxwell . |
| 4,840,623 | 6/1989 | Quackenbush . |
| 4,887,996 | 12/1989 | Bengmark . |
| 4,925,445 | 5/1990 | Sakamoto et al. . |
| 4,927,426 | 5/1990 | Dretler . |
| 4,928,694 | 5/1990 | Maxwell . |
| 4,934,369 | 6/1990 | Maxwell . |
| 4,951,669 | 8/1990 | Maxwell et al. . |
| 5,168,873 | 12/1992 | Seifert et al. ...................... 128/684 |

FOREIGN PATENT DOCUMENTS

| | | |
|---|---|---|
| 0132344A3 | 1/1985 | European Pat. Off. . |
| 0276977 | 1/1988 | European Pat. Off. . |
| 0276977A2 | 8/1988 | European Pat. Off. . |
| 0347170A1 | 12/1989 | |
| 0468616A2 | 4/1991 | European Pat. Off. . |
| 2639237 | 11/1988 | France . |
| WO86/03956 | 7/1986 | PCT Int'l Appl. . |
| 0343094 | 1/1989 | PCT Int'l Appl. . |

OTHER PUBLICATIONS

Mahutte et al., "Progress In The Development Of A Fluorescent Intravascular Blood Gas System In Man," Journal of Clinical Monitoring, vol. 6, No. 2, p. 147, Apr. 1990.

Pieper et al., "Catheter Tip Gauge For Measuring Blood Flow Velocity And Vessel Diameter In Dogs," Journal of Applied Physiology, vol. 24, No. 2, p. 259, Feb. 1968.

Gehrich et al., "Optical Fluorescence And Its Application To An Intravascular Blood Gas Monitoring System," IEEE Transaction On Biomedical Engineering, vol. BMee-33, No. 2, Feb. 1986, pp. 117–132.

Tusa et al., "Fiber Optic Microsensor For Continuous In-Vivo Measurement Of Blood Gases," Cardiovascular Devices, Inc., 2801 Barranca Road, Irvine, California 92714, SPIE vol. 713 Optical Fibers In Medicine II (1986), pp. 137–143.

Mahutte et al., "Progress In The Development Of A Fluorescent Intravascular Blood Gas System In Man," Letter to the Editor by Barry A. Shapiro, MD, Reply by: C. Kees Mahutte, MD, PhD; Journal of Clinical Monitoring, vol. 7, No. 2, Apr. 1991, p. 212.

Barker et al., "Continuous Fiberoptic Blood-Gas Monitoring: A Comparison of 18 and 20 Gauge Arterial Cannulas," ASA Abstracts Anesthesiology, vol. 71, No. 3A, Sep. 1989, Item No. A377.

Primary Examiner—Lee S. Cohen
Assistant Examiner—Robert L. Nasser Jr.
Attorney, Agent, or Firm—Wolf, Greenfield & Sacks

[57] ABSTRACT

Apparatus and method for positioning a probe through a catheter wherein a sensing element on the probe is located outside the catheter but is spaced from the luminal surface of the blood vessel to prevent any adverse effect on the sensor measurement. A standard introducer catheter may be used and a support tube is provided around a portion of the probe and is slidably engagable within the catheter lumen for positioning the probe against an anterior wall of the catheter, away from a posterior vessel wall on which the catheter lies. In a second embodiment, a portion of the support tube extends outside the distal end of the catheter to prevent any possible contact between the sensing element and posterior vessel wall.

22 Claims, 4 Drawing Sheets

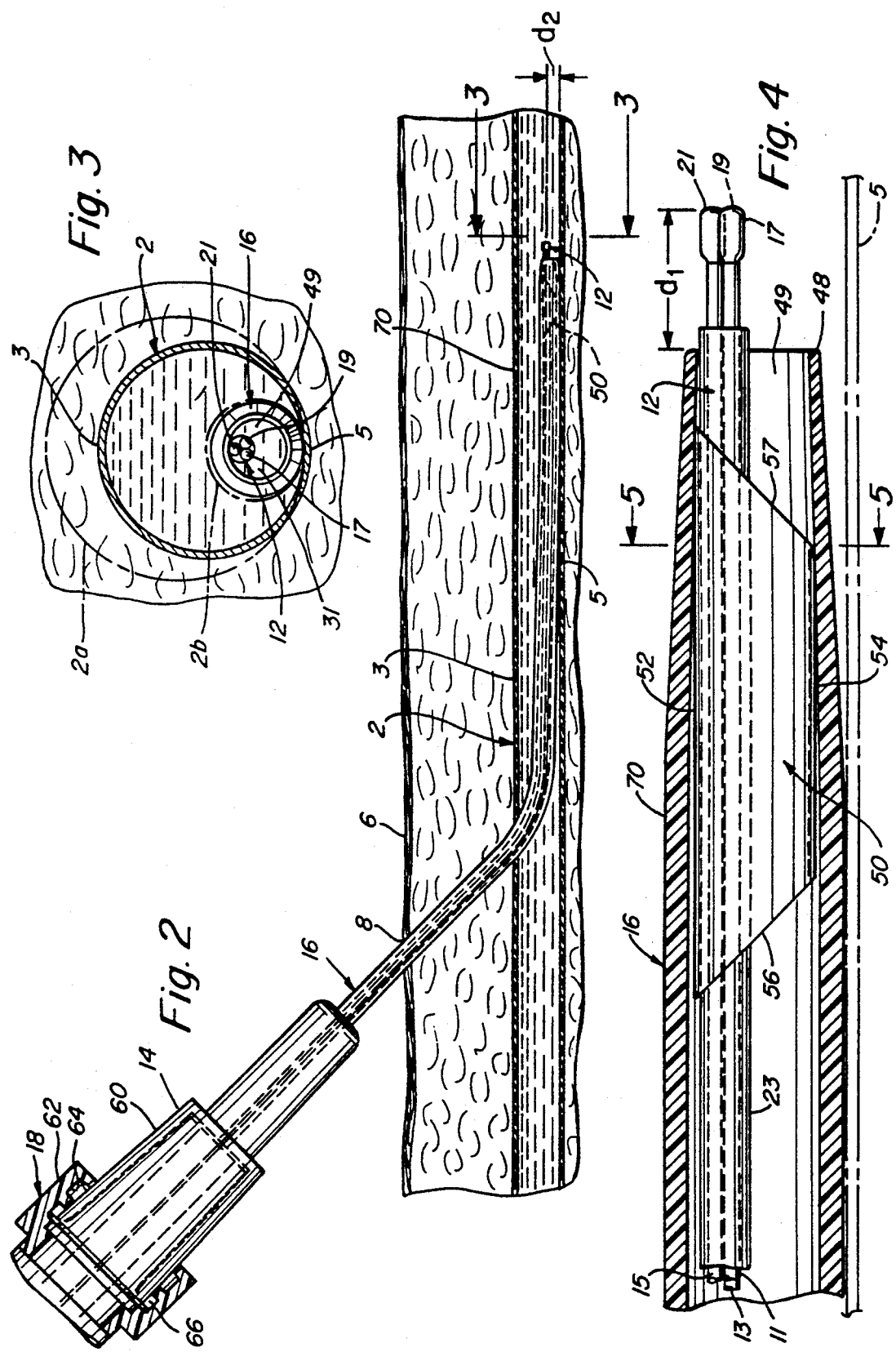

APPARATUS AND METHOD FOR POSITIONING A SENSOR AWAY FROM THE BLOOD VESSEL WALL

FIELD OF THE INVENTION

This invention relates to an in vivo probe, such as an optical probe having sensors for continuously monitoring the parameters of oxygen, carbon dioxide, and pH. In particular, it relates to a device and method for positioning such a blood gas probe in the radial artery with the sensors spaced from the luminal surface of the artery to prevent the occurrance of adverse effects on the sensor response.

BACKGROUND OF THE INVENTION

It is often desirable during medical diagnostic procedures to monitor the patient's blood on a continuous basis for such characteristics as the concentrations of oxygen ($O_2$) and carbon dioxide ($CO_2$), and the pH level. Considerable research and development efforts have been directed to in vivo sensing devices that can be delivered to and placed directly in the patient's artery to expose the sensor to blood flowing in that artery. Such continuous in vivo sensing provides a real time monitoring of the patient's condition and is preferred, in many cases, to a batch processing in which a predetermined sample volume of blood is removed and tested outside the bloodstream.

A variety of blood gas sensing devices have been proposed, typically in the form of an optical probe that incorporates a light transmissive optical fiber having a sensing element at the distal end of the fiber. By way of example, a number of such sensing devices are described in "Progress in the Development of a Fluorescent Intravascular Blood Gas System In Man", C. K. Mahutte et al., *Journal of Clinical Monitoring*, Vol. 6, No. 2, April 1990, pp. 147-157, and J. L. Gehrich et al., "Optical Fluorescence and Its Application to an Intravascular Blood Gas System", *IEEE Trans. Biomed. Eng.*, vol. 2, 1986, pp. 117-132, the disclosures of which are hereby incorporated by reference in their entirety. Reference also is made to U.S. Pat. No. 4,830,013 (issued May 16, 1990) and U.S. Pat. No. 4,951,669 (issued Aug. 28, 1990), both to Maxwell et al., for further descriptions of such probes.

Typically, it has been proposed to insert a blood gas sensor into an artery, such as the radial artery, in the region of the wrist. Access to the radial artery is convenient in that it is common to catheterize hospital patients with a short catheter accessing the radial artery for measuring blood pressure. It would be desirable to insert a blood gas sensor probe through that same catheter, thus avoiding the necessity of making a second percutaneous puncture.

Although considerable progress is believed to have been made in the development of the technology of the sensors themselves, significant difficulties have been encountered in using such sensors to measure the blood parameters under investigation. Although it would be desirable to be able to measure the blood parameters directly and continuously within the artery, attempts to do so frequently have resulted in aberrant, erratic sensor values. A number of hypotheses have been developed to explain the cause of the aberrant sensor values, among which is one referred to in the Mahutte publication as the "wall effect", said to be caused by the sensor touching the blood vessel wall and hence resulting in a reading of an average of blood and tissue rather than of the blood alone. Also suggested as a possible cause for the aberrant sensor values has been clotting at the probe tip. It was stated in Mahutte that when the probe tip was retracted within the delivery catheter and no longer touched the arterial wall, certain aberrations in sensed values were allegedly eliminated. However, retraction of the probe within the cannula tip causes many other difficulties. In an attempt to measure oxygen with the probe tip retracted in the cannula, it was necessary to withdraw a sample of the blood into the cannula to contact the tip of the retracted sensor. Thus, the sensing is not continuous but, instead, is periodic as a "batch" of blood is drawn into the cannula into contact with the sensor. Further, the blood inside the cannula may not have the same parameters as the blood flowing in the artery, especially when it becomes mixed with saline or other fluids which pass through the cannula. The result is an inaccurate measurement and a long response time. Additionally, retraction of the sensing probe within the catheter tip interferes with fluid communication through the catheter and has a damping effect on blood pressure readings. Still further it may cause clotting. Thus, the proposed solution in Mahutte, of retracting the probe within the catheter, has not been found acceptable.

It would be desirable, therefore, to provide an improved system by which a probe sensor may be placed within the artery so as to be presented to a continuous flow of blood, but in a manner in which the probe sensor is spaced substantially from the inner surface of the blood vessel wall, in order to accurately measure a parameter of the blood. It is among the objects of the invention to provide such a system.

Another object is to provide such a system which allows a probe to be positioned through a catheter without substantially effecting the taking of blood pressure measurements.

Yet another object is to provide such a system which prevents thrombus formation.

A still further object is to provide a system for positioning any type of probe spaced from a body member.

SUMMARY OF THE INVENTION

The present invention is designed to allow placement of a multi-parameter probe (e.g., for measuring $O_2$, $CO_2$ and pH) in a radial artery with the sensing elements positioned away from the artery wall. Some of the principal benefits of the invention, aside from insuring accurate measurement, are its simplicity, low cost of manufacture, and ability to be used with a standard radial artery introducer catheter.

There is a natural tendency for a percutaneously placed catheter to lie against the posterior wall of the radial artery. Thus, when an introducer catheter is inserted into the radial artery in a patient's arm, it assumes the shape shown in FIG. 1a. The distal tip 201 of the catheter 200 is naturally forced against the arterial wall opposite the point of insertion, referred to as the posterior (or lower) vessel wall 202. This is a result of the catheter insertion angle and the longitudinal relationship of the artery to the skin surface. The bottom wall of the catheter thus rides along the posterior vessel wall as the catheter is further advanced into the artery 203. Without the support means of this invention, the sensor probe 204 would also lie against the bottom wall of the introducer catheter and thus on the posterior vessel wall when it exits the distal end of the catheter.

The anterior wall of the catheter will generally be in the vicinity of the centerline of the artery, given the relative diameters of the radial artery and catheter. If a sensor could be reliably forced against the anterior wall of the catheter, it also would be near the centerline of the artery, and away from both the anterior and posterior walls. However, it is also important to maintain the fluid dynamic aspects of the system while insuring placement of the sensor.

Although not intending to be bound by any particular mechanism, it is believed that the adverse effect on sensor response which occurs when a sensor is placed along the vessel wall may be due to a dynamic flow effect wherein the flow of different solutes through the blood may interfere with one another. More specifically, blood flowing through an artery contains a first solute, dissolved oxygen gas ($O_2$), and a second solute, dissolved carbon dioxide gas ($CO_2$). The $CO_2$ from adjacent tissue is continuously entering the artery in a transverse or radial direction across the wall because the concentration of $CO_2$ is much higher outside of the artery. There is a decreasing concentration gradient going across the artery wall and this gradient causes a flow of $CO_2$ across the wall. If the $CO_2$ encounters an oxygen sensor adjacent to the wall, the flow of $CO_2$ will act to remove oxygen from within the sensor and thus depress the sensor measurement of oxygen. Moving away from the artery wall and further into the artery, the $CO_2$ flow decreases so that there is no longer a net flow and thus no longer an effect on the oxygen sensor reading. There may be a complementary effect caused by the flow of $O_2$ on the measurement of a carbon dioxide sensor. In effect, the higher $O_2$ concentration within the artery may cause a flow of $O_2$ across the artery wall to the outside. However, one would expect this effect to be smaller because the relative amount of $O_2$ is much less.

In accordance with this invention, a thin-walled support tube is provided around the sensor probe. The tube has an outer diameter which permits it to be slidably engaged within the introducer catheter lumen. The sensor probe is bonded to the top inner wall of the support tube and the top walls of the support tube and catheter are aligned so that the sensor tip is spaced from the posterior vessel wall when it exits the catheter. The thin walled tube presents little interference to the fluid path and the tube lumen becomes the main fluid path for the system—allowing sample aspiration, infused flushes and transmission of pressure waveforms. The tube presents no additional surfaces for thrombus formation. The proximal and distal ends of the support tube are preferably tapered to facilitate movement of the combined probe and support tube through the catheter lumen. The distal tip of the probe is positioned outside the catheter, a fixed distance from the distal tip of the catheter, by engaging luer fittings on the proximal ends of the catheter and probe.

In an alternative embodiment, the support tube includes a lower wall portion or shield which extends outside the distal end of the catheter to prevent any possible contact between the sensor tip and vessel wall. Thus, if for some reason the catheter tip were to tend to sink into the vessel wall over time, the shield would prevent the sensor from contacting the vessel wall. The combined shield and support tube may also be provided as a helical ribbon, as opposed to a cylindrical tube, wherein the ribbon is wrapped around and bonded to the probe at its proximal end. The front edge of the ribbon is rounded to eliminate any sharp edges and to ease insertion. The ribbon may act like a spring which can be compressed around the probe to make it easier to insert into the catheter and which will spring into position, if for example the ribbon were made from a heat activated material which would expand upon contact with the higher temperature of the blood.

It is a significant feature of this invention that the sensor may be positioned outside of the introducer catheter and thus directly in the blood vessel to ensure accurate measurement, while still preventing contact of the sensor and vessel wall. It has been found that prior devices in which the sensor is disposed within the catheter (in order to prevent contact with the vessel wall) do not allow accurate, real time measurement of the blood gas partial pressure.

More generally, the invention can be used for inserting any type of probe through a catheter lumen and into the body where it is desired to space the distal end of the probe from a body member. Thus, the invention includes a support member attached to the probe to form a probe assembly which can be slidably engaged within a catheter lumen and which positions a probe along one wall of the catheter lumen. The support member maintains a fluid flow path through the catheter lumen. When the catheter lies with its other wall (opposite the one wall along which the probe is positioned) in contact with a body member, the distal end of the probe exiting the catheter will be spaced from the body member. The invention also includes the method of positioning the probe assembly through the catheter and into the body. The body member may be other than a blood vessel, including any intraluminal space or channel, orifice, or cavity. The probe may be other than for measuring a parameter of the blood, such as an electrical probe for transmitting electrical signals to or from the body, or some other type of optical, chemical, or sampling probe for viewing, monitoring, or interacting with the body.

BRIEF DESCRIPTION OF THE DRAWINGS

FIG. 2 is a cross-sectional view taken along the section lines 2—2 of FIG. 1 showing the catheter and probe of this invention positioned in the radial artery with the probe tip spaced from the artery wall.

FIG. 3 is a cross-sectional view, taken along the section lines 3—3 of FIG. 2, showing the catheter, support tube and probe positioned within the artery, with certain alternative artery diameters shown in phantom lines.

FIG. 4 is a partial cross sectional view showing the distal tip of the catheter with the probe and support tube positioned therein.

DETAILED DESCRIPTION OF THE PREFERRED EMBODIMENTS

Figure 1:
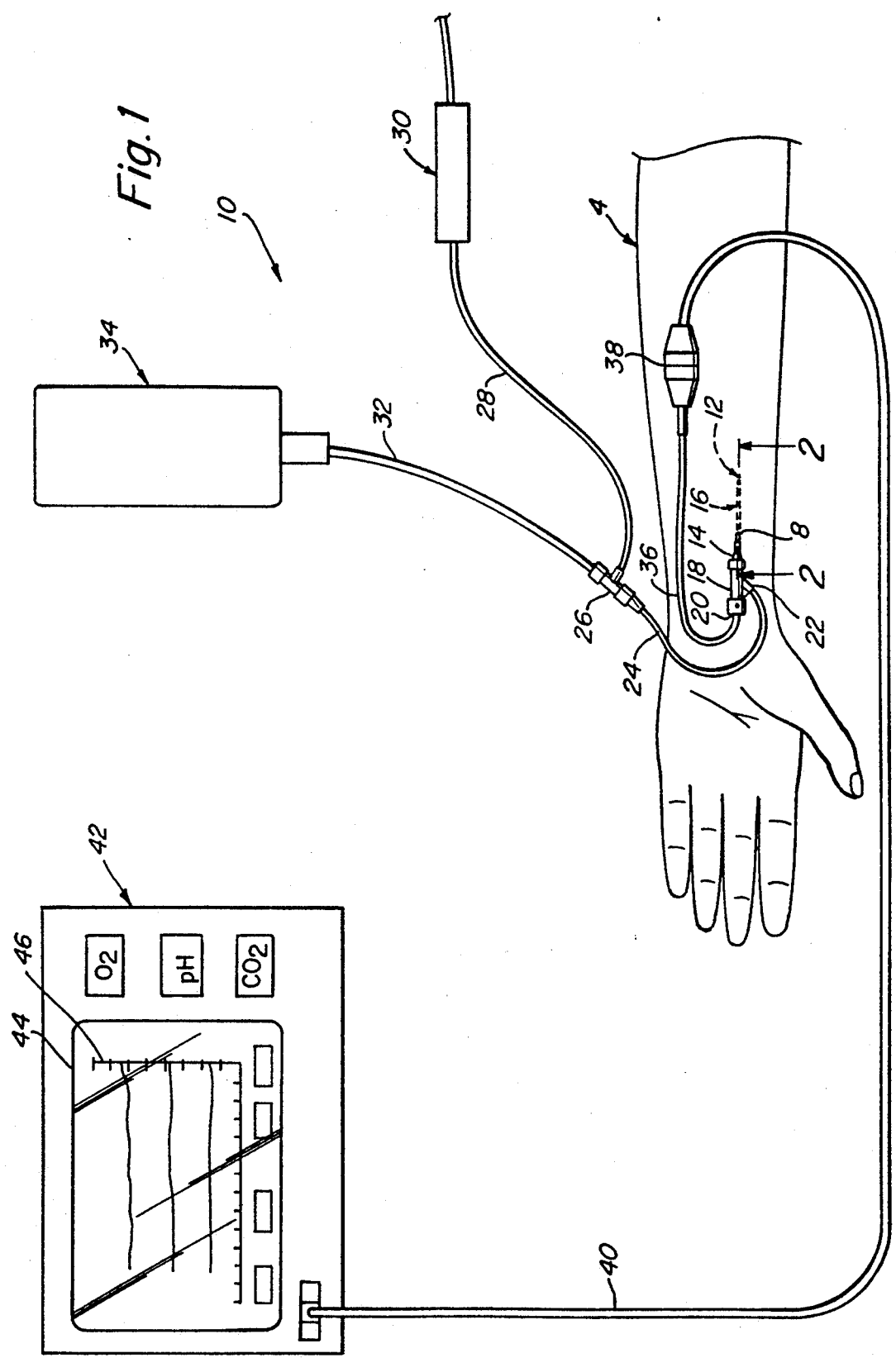
FIG. 1 is a diagrammatic illustration of a system for continuous in vivo measurement of various parameters of the blood, which includes the apparatus and method of this invention for spacing a sensor outside the catheter but away from the luminal surface of the artery.
Figure 1A:
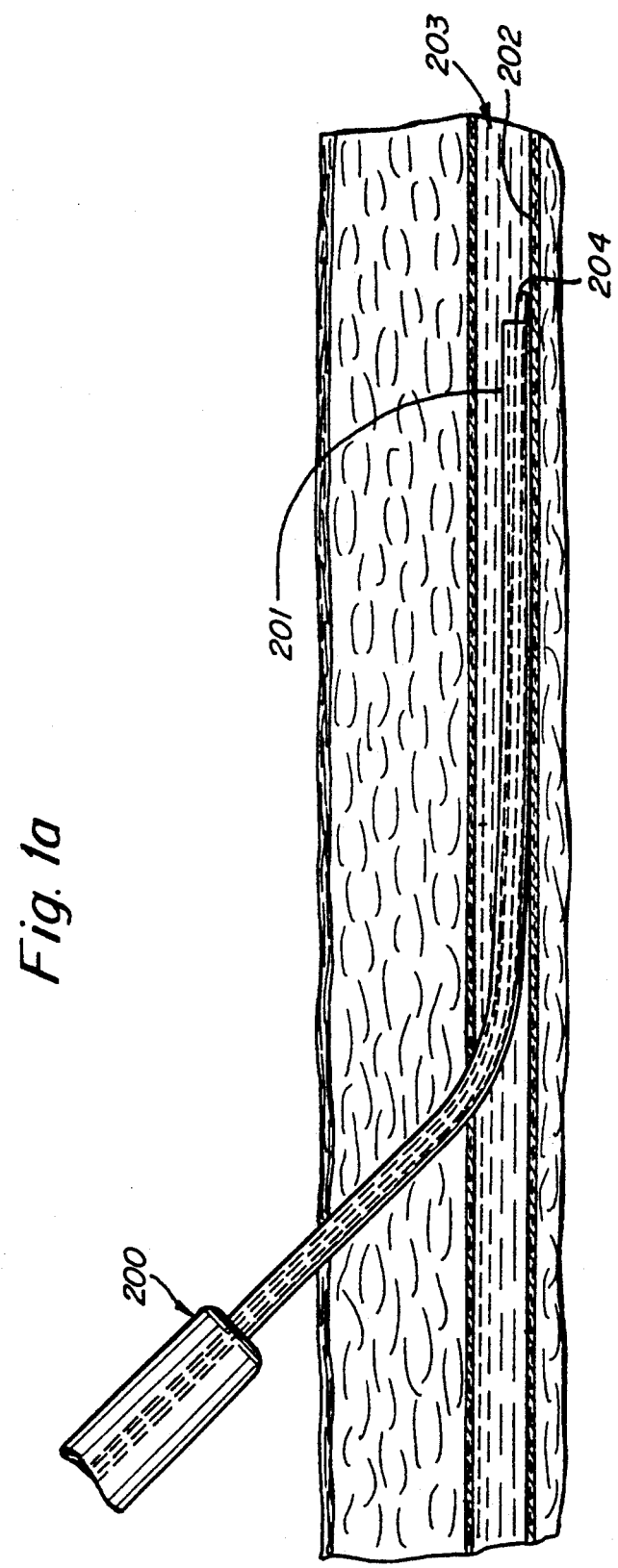
FIG. 1a is an illustration showing how a typical probe and catheter assembly, without the positioning means of this invention, rides along the posterior wall of the radial artery such that the probe contacts the artery wall when it exits the catheter.

FIG. 1 shows a system 10 for continuous in vivo blood gas monitoring in which an optical sensor probe 12 is positioned in the radial artery of a patient's forearm 4. The indwelling portions of the probe 12 and introducer catheter 16, shown in dashed lines, are positioned in the patient's radial artery and exit through the skin 6 (see FIG. 2) from an insertion site 8. Moving proximally from the insertion site 8, a proximal end 14 of the introducer catheter 16 is attached to a Y-body fitting 18. The Y-body 18 has a main lumen and proximal port 20 through which the probe passes, and a secondary side branch off the main lumen terminating at port 22, to which a fluid line 24 is attached. The fluid line 24 branches into two sections at a stop cock connection 26, the first branch 28 being connected to a pressure transducer 30 for measuring the patient s blood pressure, and a second fluid line branch 32 being connected to a source 34 of fluid, such as a saline solution for flushing the system. The outer probe sheath 36 exiting from port 20 of the Y body contains optical fibers for transmitting signals to and from the sensing means at the distal end of the probe, and has an optical/electrical connector 38 at its distal end for connection via an electrical line 40 to a monitor 42. The monitor has a display screen 44 with a graphical overlay 46 for presenting a continuous display of the partial pressures of oxygen ($O_2$) and carbon dioxide ($CO_2$), as well as pH, in graphical as well as digital display forms.

The positioning apparatus of this invention is designed to position the sensing means at the distal end of the probe a fixed distance from the distal tip of the catheter and spaced from the luminal surface of the radial artery. A first embodiment, as shown in FIGS. 2-5, includes a support tube 50, comprising a hollow cylindrical wall portion having a central lumen 31. Tube 50 has attached to its upper lumen surface the probe 12, and the combined tube and probe are positioned within the catheter 16 adjacent its distal end 48. The probe 12 consists of three optical fibers 11, 13, and 15, having separate sensing elements 17, 19, and 21 on their distal ends for $O_2$, $CO_2$ and pH, respectively. The fibers are housed within a polymer sheath 23 for protecting the delicate fibers. The sheath 23 is connected at a proximal portion to the Y-body 18, as described hereinafter, for the purpose of precisely positioning the distal tip of the probe a fixed distance $d_1$ from the distal tip of the catheter.

Figure 5:
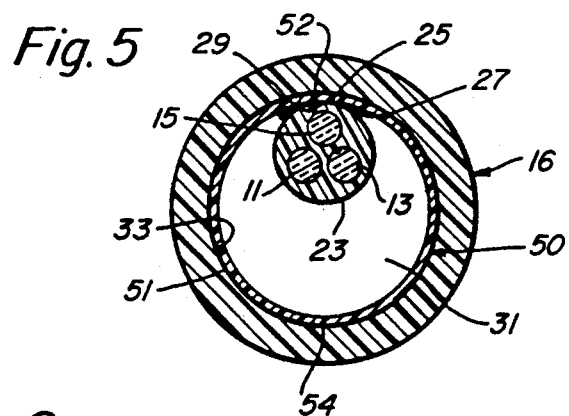
FIG. 5 is a cross sectional view, taken along the section lines 5—5 in FIG. 4, showing the probe, support tube and catheter, with the probe adhered to the upper wall of the support tube.

As shown in FIG. 5, the upper wall surface 25 of probe sheath 23 is attached by adhesive 27 to upper wall surface 29 of the tube support lumen 31, leaving the remaining lower portion of the tube support lumen free to serve as a fluid flow path through both the tube 50 and catheter 16. Preferably, at least about one third of the tube lumen, and more preferably about two thirds, is left open to serve as the fluid flow path. The outer diameter (OD) 51 of the support tube is sized to slidably engage the inner diameter (ID) 33 of the catheter adjacent its distal end 48. The lumen 49 of the catheter may taper inward slightly at the distal end to provide a reduced profile for eased insertion into the blood vessel.

As shown in FIG. 4, preferably the upper wall 52 of the tube support is longer than the lower wall 54, such that the longer support wall 52 is provided adjacent the probe sheath 23 for improved adhesion and support, and the support tube tapers inwardly towards the shorter lower tube wall 54 to ease insertion of the support tube and probe into the catheter. The proximal 56 and distal 57 edges taper going from the upper wall 52 to the lower wall 54. The fitting 18 has a dot 72 (see FIG. 1) to facilitate aligning the upper wall 52 of the support tube along the anterior wall 70 of the catheter.

By way of example, in applicant's preferred embodiment a standard "Jelco" (registered trademark of Critikon, Inc., Tampa, Fla.) radial introducer catheter can be used having an outer diameter (OD) of 0.033". A three sensor probe 12 has an approximate OD of 0.010-0.012" and resides within a support tube 50 having an OD of 0.028" and an ID of 0.0265". The top (long) length 52 of the support tube is 0.100-0.150" and the bottom (tapered) length 54 of the support tube is 0.075". The support tube is formed of a bio compatible polyimide material which provides sufficient strength in a relatively thin wall thickness to support the probe, while remaining sufficiently flexible to ease insertion and prevent breakage of the probe assembly. While the support tube is preferably made of polyimide tubing having a wall thickness of about 0.001" or less, any other biocompatible material may be used of sufficient body or rigidity to position and support the probe, in spite of the very thin wall thickness. If the support tube material is too stiff, it may cut the catheter, or in the shield embodiment described hereinafter (wherein a portion of the support tube resides outside the catheter), it may cut into the artery itself. The probe 12 may be bonded by acrylic resin to the top wall 52, of the support tube lumen.

The standard introducer catheter 16 has a female connector at its proximal end 14 which receives a male fitting on the distal end 60 of the Y-body. An outer luer fitting 62 is provided on the distal end of the Y-body with interior threads 64 for engaging opposing lugs 66 on the proximal end of the introducer catheter. The probe is attached to the Y-body to prevent axial movement. The engagement of the introducer catheter and Y-body at the luer fitting 62 and predetermined lengths of the probe and catheter insures that the distal tip of the probe is positioned a fixed distance $d_1$ from the distal tip of the catheter. The sheathed optical fibers 11, 13, 15 of the probe pass through the main lumen of the Y-body, while the secondary branch of the Y-body also allows fluids to pass through the main lumen.

As shown in FIGS. 3 and 4, the probe lies along the upper or anterior wall 70 of the catheter (the anterior wall being closest to the surface of the skin 6 which serves as the insertion site 8). The probe tip is thus spaced a distance $d_2$ from the posterior artery wall 5. Because the catheter 16 has a substantially smaller outer diameter than the inner diameter of the artery 2, the probe 12 is likewise spaced from the anterior wall 3 of the artery. As shown in FIG. 3, an ample fluid flow path is provided through the remaining portion of the support tube lumen 31 along the posterior wall 54 of the tube enabling accurate blood pressure measurements to be taken via pressure transducer 30, and to allow the infusion of flush solutions or other medicated fluids into the artery, or extraction of blood samples as necessary.

FIG. 3 shows the approximate dimensions of the probe 12 and catheter 16 in a nominal sized radial artery 2, the artery having an OD of about 2.37 millimeters (mm) and being positioned below the skin about 6.12 mm. This probe and catheter combination also functions properly in both the high and low ranges of artery dimensions. As shown in phantom lines in FIG. 3, a high artery profile 2a would have a diameter of about 3.1 mm. A low artery profile 2b would have a diameter of about 1.2 mm. The radial artery is spaced from about 2.7 mm to about 11.2 mm from the surface of the skin. In all cases, the probe would be positioned a sufficient distance from the anterior 3 and posterior 5 walls of the artery to prevent undesirable wall effects.

Figure 6:
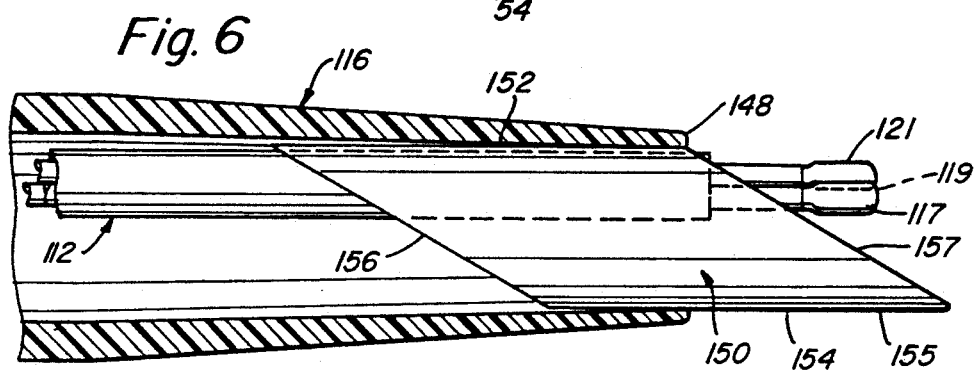
FIG. 6 is a partial sectional view of the distal tip of the catheter showing an alternative embodiment wherein the support tube includes a portion extending outside the distal tip of the catheter, which serves as a shield.

In a second embodiment shown in FIG. 6, the support tube 150 includes a portion 155 which extends outside the distal end 148 of the catheter 116 to serve as a shield which prevents contact between the sensors 117, 119 and 121 and posterior wall of the artery in event that the patient's arm is moved or the catheter is positioned in such a way that the probe 112 may contact the posterior artery wall. This embodiment is similar to the previously described embodiments in terms of materials and attachment of the probe sheath to the support tube. However, in this embodiment the support tube 150 is shaped as a diagonally excised portion of a tubular element, wherein the proximal 156 and distal 157 edges are parallel and taper distally going from the upper wall 152 to the lower wall 154 of the support tube.

Figure 7:
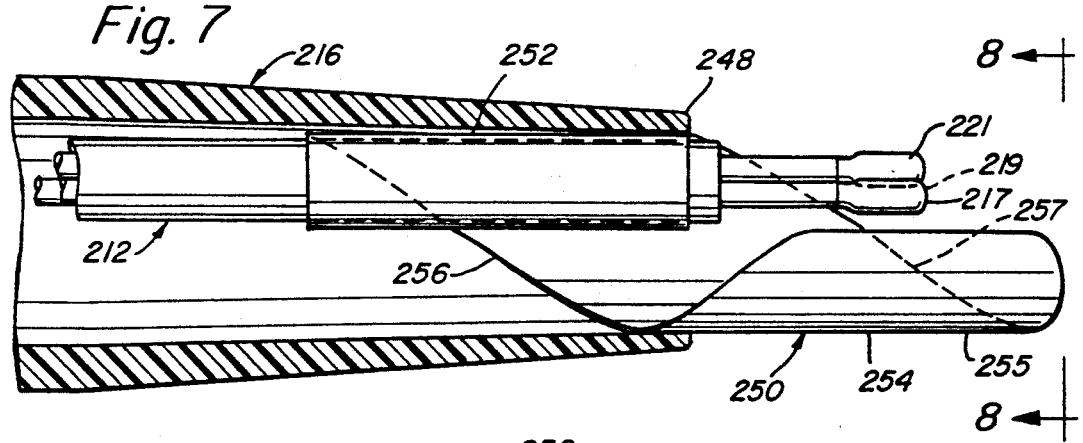
FIG. 7 is a partial sectional view of the distal tip of the catheter showing a further alternative embodiment of the support tube and shield, comprising a helical ribbon or coil.
Figure 8:
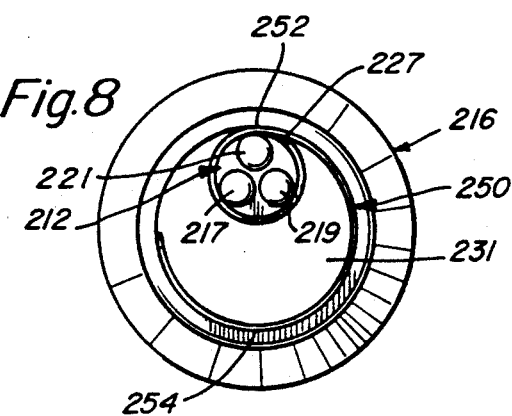
FIG. 8 is an end view as seen along the section lines 8—8 in FIG. 7, showing the catheter, probe, and helical support tube and shield, with the probe adhered to the upper end of helical ribbon.

In a further alternative embodiment shown in FIGS. 7 and 8, a helical member 250 is provided as a support tube (as used herein "support tube" includes a helical ribbon or coil), wherein at its upper end 252 the helical member has a smaller diameter portion which is wrapped 360° around the probe sheath 212 and attached thereto via adhesive 227, whereas the remaining portion of the helical support has a greater radial diameter and engages the inner lumen of the catheter 216 to provide a flow path 231. Again, the proximal 256 and distal 257 edges of the helical member are parallel and taper distally; the bottom end 254 is rounded to ease insertion and prevent injury to the catheter or artery wall. A portion 255 extends outside the distal end 248 of the catheter.

While this invention is not limited to any particular sensing element, the optical sensors for $CO_2$ and $O_2$ described in U.S. Pat. No. 4,800,886 issued Jan. 1, 1989) to Nestor et al. and U.S. Pat. No. 4,861,727 (issued Aug. 8, 1989) to Hauenstein et al. would be suitable and these patents are hereby incorporated by reference in their entirety. In addition, other types of sensors, such as ion sensors for measuring potassium, calcium, or sodium ions, may be provided on the probe.

It will be appreciated that still other configurations of the support tube, and combined support tube and shield, may be provided so as to position the sensor within the artery at a spaced location from the luminal surface of the artery. Thus, the foregoing discussion of the invention is intended merely to be illustrative thereof and other embodiments, modifications and equivalents may be apparent to those skilled in the art without departing from its spirit.

Having thus described the invention what is desired to be claimed is:

1. A probe assembly for inserting a probe through a lumen of a catheter and into a blood vessel, while maintaining a flow path through a catheter and positioning a distal end of the probe at a location spaced from a luminal surface of the blood vessel, wherein the catheter tends to lie along a lower vessel wall opposite a site of insertion, the probe assembly comprising:
 a probe having means for sensing a parameter of the blood;
 a support tube having an outer diameter sized to be slidably engaged within the catheter lumen and a tube lumen which forms a fluid flow path through both the tube and catheter;
 the probe being disposed within the tube lumen and attached to an upper tube wall portion while maintaining the flow path along a lower tube wall portion;
 wherein the upper wall portion of the support tube may be aligned along an upper wall of the catheter so that the probe is spaced from said lower wall of the vessel.

2. The probe assembly of claim 1, wherein the probe is an optical probe.

3. The probe assembly of claim 1, wherein the sensing means is adapted for measuring a blood parameter selected from the group consisting of oxygen, carbon dioxide, pH, and ion concentration.

4. The probe assembly of claim 1, wherein the sensing means is disposed at the distal end of the probe.

5. The probe assembly of claim 1, further comprising means for positioning the distal end of the probe a fixed distance from a distal end of the catheter.

6. The probe assembly of claim 1, wherein the support tube has tapered ends to ease insertion through the catheter lumen.

7. The probe assembly of claim 1, further comprising a Y-body having a main lumen in which a proximal end of the probe is positioned and a secondary lumen for fluids.

8. The probe assembly of claim 1, wherein the tube is a cylindrical member.

9. The probe assembly of claim 1, wherein the support tube has diagonally tapered ends between the upper and lower wall portions, and the upper wall portion is longer than the lower wall portion.

10. The probe assembly of claim 1, wherein the support tube includes a lower shield portion positionable outside the catheter lumen which prevents the distal end of the probe from contacting the lower wall of the vessel.

11. The probe assembly of claim 10, wherein the support tube has tapered ends.

12. The probe assembly of claim 10, wherein the support tube is a helical member.

13. The probe assembly of claim 12, wherein the helical member has an upper portion of lesser diameter engaging the probe and a lower portion of greater diameter for engaging the catheter lumen.

14. The probe assembly of claim 13, wherein the helical member has rounded ends.

15. The probe assembly of claim 10, wherein the support tube has parallel diagonally tapered ends between the upper and lower wall portions.

16. A system for inserting a probe through a lumen of a catheter and into a blood vessel, while maintaining a flow path through the catheter and positioning a distal end of the probe at a location spaced from a luminal surface of the blood vessel, the system comprising:

a catheter which when passed through an insertion site tends to lie along a lower vessel wall opposite the site of insertion;

a probe having means for sensing a parameter of the blood;

a support tube having an outer diameter sized to be slidably engaged within the catheter lumen and a tube lumen which forms a fluid flow path through both the tube and catheter;

the probe being disposed within the tube lumen and attached to an upper tube wall portion while maintaining the flow path along a lower tube wall portion;

wherein the upper wall portion of the support tube may be aligned along an upper wall of the catheter so that the probe is spaced from said lower wall of the vessel.

17. The system of claim 16, further comprising:

a fitting to which a proximal portion of the probe is attached, said fitting having a releasable attaching means for connecting the fitting and catheter such that the distal end of the probe is positioned a fixed distance from a distal end of the catheter.

18. The system of claim 17, wherein the fitting is a Y-body having a main lumen through which the probe passes and a secondary lumen for fluids.

19. The system of claim 16, wherein the catheter is sized for use in the radial artery.

20. The system of claim 19, wherein the sensing means is adapted for measuring a blood parameter selected from the group consisting of oxygen, carbon dioxide, pH, and ion concentration.

21. A method for inserting a probe within a blood vessel at a location spaced from a luminal surface of the vessel, comprising the steps of:

providing a probe assembly as defined in claim 1;

inserting a catheter having a lumen through an insertion site and into a blood vessel, wherein the catheter tends to lie along a lower vessel wall opposite the site of insertion; and advancing the probe through the catheter lumen so that the probe emerges from a distal end of the catheter and is spaced from a lower wall of the vessel.

22. A probe assembly for inserting a probe through a lumen of a catheter and spaced from a body member comprising:

a probe;

a support member attached to the probe to form said probe assembly which is slidably engagable within said catheter lumen and maintains the probe along one wall of the catheter lumen and a distal end of the probe outside a distal end of the catheter, such that when another wall of the catheter, opposite the one wall along which the probe is maintained, lies in contact with a body member, the distal end of the probe is spaced from the body member, wherein the support member comprises a tube having an outer diameter sized to slidably engage the catheter lumen and a tube lumen which forms the fluid flow path through the catheter lumen.

* * * * *